(12) United States Patent
Mach et al.

(10) Patent No.: US 8,828,682 B2
(45) Date of Patent: Sep. 9, 2014

(54) METHODS AND ARTICLES FOR DETECTING HEMOLYTIC MICROORGANISMS

(75) Inventors: Patrick A. Mach, Shorewood, MN (US); Michelle L. Rosauer, North St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 380 days.

(21) Appl. No.: 13/133,456

(22) PCT Filed: Dec. 8, 2009

(86) PCT No.: PCT/US2009/067059
§ 371 (c)(1), (2), (4) Date: Jun. 8, 2011

(87) PCT Pub. No.: WO2010/077619
PCT Pub. Date: Jul. 8, 2010

(65) Prior Publication Data
US 2011/0244511 A1    Oct. 6, 2011

Related U.S. Application Data (60) Provisional application No. 61/120,862, filed on Dec. 9, 2008.

(51) Int. Cl.
*C12Q 1/04* (2006.01)
*C12Q 1/02* (2006.01)
*C12Q 1/06* (2006.01)

(52) U.S. Cl.
CPC ........................................ *C12Q 1/04* (2013.01)
USPC ................................... 435/39; 435/4; 435/34

(58) Field of Classification Search
USPC ................................................. 435/4, 34, 39
See application file for complete search history.

(56) References Cited

U.S. PATENT DOCUMENTS

| | | | |
|---|---|---|---|
| 3,445,339 A | 5/1969 | Controni et al. | |
| 4,565,783 A | 1/1986 | Hansen et al. | |
| 5,137,812 A | 8/1992 | Matner | |
| 5,232,838 A | 8/1993 | Nelson et al. | |
| 5,635,367 A | 6/1997 | Lund | |
| 5,681,712 A | 10/1997 | Nelson | |
| 5,837,482 A | 11/1998 | Mach et al. | |
| 6,022,682 A | 2/2000 | Mach et al. | |
| 6,130,057 A * | 10/2000 | Gosnell et al. | 435/32 |
| 6,331,429 B1 | 12/2001 | Ushiyama | |
| 7,018,828 B1 * | 3/2006 | Taintor | 435/253.6 |
| 7,183,073 B2 * | 2/2007 | Hyman et al. | 435/29 |
| 7,223,364 B1 | 5/2007 | Johnston et al. | |

FOREIGN PATENT DOCUMENTS

| | | |
|---|---|---|
| WO | WO 01/59060 | 8/2001 |
| WO | WO 2004/027086 | 4/2004 |
| WO | WO 2004/033714 | 4/2004 |

OTHER PUBLICATIONS

Atlas et al. 1997. Handbook of Microbiological Media, Second edition, CRC Press, Boca Raton, p. 361.*

Singleton et al. 1991. Dictionary of Microbiology and Molecular Biology, Second edition, A Wiley Interscience Publication, John Wiley & Sons , Chichester, p. 847.*

* cited by examiner

*Primary Examiner* — Jon P Weber
*Assistant Examiner* — Kailash C Srivastava

(57) ABSTRACT

A thin film culture plate device useful for detecting hemolysin-producing microorganisms is included. The device can further include selective agents and/or indicators to differentiate groups or species microorganisms. Methods of use include detecting or enumerating hemolysin-producing microorganisms.

9 Claims, 2 Drawing Sheets

METHODS AND ARTICLES FOR DETECTING HEMOLYTIC MICROORGANISMS

CROSS REFERENCE TO RELATED APPLICATIONS

This application claims the benefit of U.S. Provisional Patent Application No. 61/120,862, filed Dec. 9, 2008.

BACKGROUND

A variety of specimens (e.g., clinical, environmental, food, processing equipment) are routinely tested to determine whether they contain microorganisms. Clinical samples such as urine, sputum, wound exudate, and the like, may have come in contact with skin or mucous membranes and can contain a variety of microorganisms. Some of the microorganisms in clinical samples are considered to be normal inhabitants of the skin or mucous membrane environment. Other microorganisms are considered pathogenic and can be associated with infectious disease processes.

Typically, one of the first steps in evaluating a specimen for viable pathogenic microorganisms is to grow the microorganisms to obtain large enough numbers to perform subsequent genetic, immunological, biochemical, and/or microscopic analyses. Often, the first step includes separating the individual microorganisms by spreading (or "streaking") the sample onto a semisolid agar growth medium. This process results in the formation of individual, isolated colonies that can be used for subsequent testing.

Optionally, the agar growth medium on which the sample is spread can contain a differential reagent. Differential reagents can help with the classification and/or identification of the microorganisms growing on the medium. For clinical specimens, red blood cells (e.g., from a sheep or a horse) are often used as a differential reagent. Additionally, it is known in the art that components of blood (e.g., vitamins) can promote the growth of fastidious microorganisms. Certain pathogenic microorganisms, such as *Streptococcus pyogenes* and *Staphylococcus aureus*, secrete hemolysins that diffuse through the medium and lyse red blood cells, producing a distinctive zone around the colony. The hemolytic reactions can help with the early detection and identification of pathogenic microorganisms.

Production of differential semisolid medium containing red blood cells is a tedious process. The red blood cells are quite sensitive to thermal and osmotic shock, either of which can result in spontaneous lysis of the cells. The dehydrated agar is typically melted in water while mixing in a nutrient base. The mixture is subsequently sterilized by autoclaving and the temperature is lowered to a point where it is high enough to keep the agar molten but low enough to prevent the thermal lysis of the red blood cells. The mixture is then poured into containers, such as petri dishes. The agar is generally allowed to solidify before inoculating it with a sample. If the agar is not used immediately after it solidifies, typically it must be stored at refrigerator temperature and must used within several weeks because the agar begins to dehydrate and/or the red blood cells begin to spontaneously break down. If it is stored in a refrigerator, typically the agar medium is warmed to room temperature before use.

There exists a need for more convenient methods to detect hemolysin-producing microorganisms.

SUMMARY

In view of the current methods, which require considerable time and laborious steps to prepare culture medium that includes an indicator system comprising red blood cells, Applicants have recognized the need for simpler, faster methods to prepare and use a culture medium comprising red blood cells.

In one aspect, the present disclosure provides a method for detecting microorganisms. The method can comprise providing a nutrient medium comprising a cold water-soluble gelling agent, an indicator system comprising a suspension of red blood cells, and a sample suspected of containing microorganisms. The method further can comprise forming an aqueous mixture comprising the nutrient medium, the indicator system and the sample. The method further can comprise incubating the mixture for a period of time and detecting a microorganism. In some embodiments, the nutrient medium can comprise a thin film culture plate device including nutrient medium and cold-water-soluble gelling agent. In some embodiments, the method can further comprise providing a detection reagent or a selective agent, wherein forming an aqueous mixture comprises forming an aqueous mixture including the detection reagent or selective agent.

In another aspect, the present disclosure provides a method for detecting microorganisms. The method can comprise providing a nutrient medium comprising a detection reagent and a cold water-soluble gelling agent, an indicator system comprising a suspension of red blood cells, and a sample suspected of containing microorganisms. The method further can comprise forming an aqueous mixture comprising the nutrient medium, the indicator system and the sample. The method further can comprise incubating the mixture for a period of time and detecting a microorganism. In some embodiments, the nutrient medium can comprise a thin film culture plate device including nutrient medium and cold-water-soluble gelling agent. In some embodiments, the method can further comprise providing a selective agent, wherein forming an aqueous mixture comprises forming an aqueous mixture including the selective agent.

In another aspect, the present disclosure provides a method for detecting microorganisms. The method can comprise providing a nutrient medium comprising a detection reagent, a selective agent, and a cold water-soluble gelling agent; providing an indicator system comprising a suspension of red blood cells; and providing a sample suspected of containing microorganisms. The method further can comprise forming an aqueous mixture comprising the nutrient medium, the indicator system and the sample. The method further can comprise incubating the mixture for a period of time and detecting a microorganism. In some embodiments, the nutrient medium can comprise a thin film culture plate device including nutrient medium and cold-water-soluble gelling agent.

In some embodiments, detecting a microorganism can comprise detecting a hemolytic reaction. In some embodiments, detecting a microorganism can comprise counting colonies. In some embodiments, the method can further comprise a step wherein a portion of at least one colony is subjected to a supplemental test. In some embodiments, the method can include a sample that comprises a capture element.

In another aspect, the present disclosure provides a method for detecting microorganisms. The method can comprise providing i) a thin film culture plate device comprising a cold water-soluble gelling agent, ii) a nutrient medium for the growth of microorganisms, iii) an indicator system comprising a suspension of red blood cells, and iv) a sample suspected of containing microorganisms. The method further can comprise contacting the cold water-soluble gelling agent with an aqueous mixture comprising the indicator system and the nutrient medium to form a hydrated gel. The method further can comprise contacting the hydrated gel with the sample, incubating the device comprising the hydrated gel and the sample for a period of time, and detecting a microorganism. In some embodiments, the device can comprise the nutrient medium, wherein the nutrient medium is a dry nutrient medium. In some embodiments, the sample can comprise a capture agent.

In another aspect, the present disclosure provides a thin film culture plate device. The thin film culture plate device can comprise a nutrient medium comprising a cold water-soluble gelling agent and an indicator system comprising red blood cells. In some embodiments, the thin film culture plate device can further comprise a detection reagent. In some embodiments, the thin film culture device can further comprise a selective agent.

In another aspect, the present disclosure provides a kit for the detection of microorganisms. The kit can comprise a dry, rehydratable thin-film culture plate device and defibrinated blood. In some embodiments, the kit can further comprise a detection reagent. In some embodiments, the kit can further comprise a detection article. In some embodiments, the kit can further comprise a selective agent.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a sample suspected of containing "a" microorganism can be interpreted to mean that the liquid can include "one or more" microorganisms.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The invention will be further explained with reference to the drawing figures listed below, where like structure is referenced by like numerals throughout the several views.

DETAILED DESCRIPTION

Before any embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways. Also, it is to be understood that the phraseology and terminology used herein is for the purpose of description and should not be regarded as limiting. The use of "including," "comprising," "containing," or "having" and variations thereof herein is meant to encompass the items listed thereafter and equivalents thereof as well as additional items. Unless specified or limited otherwise, the terms "supported," and "coupled" and variations thereof are used broadly and encompass both direct and indirect supports and couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure is generally directed to methods and articles for detecting and differentiating microorganisms in a sample. In particular, the disclosure relates to the detection and differentiation of hemolysin-producing microorganisms in a sample. The sample can be obtained from a variety of sources. In some embodiments, the source is a clinical source. In some embodiments, the source is a food source. In some embodiments, the source is a nonfood source. In some embodiments, the microorganisms can be captured and, optionally, concentrated on or in a capture element. In contrast to conventional methods for detecting hemolysin-producing microorganisms, which require laborious procedures to prepare the growth medium (e.g., blood agar) or require the use of prepared, prehydrated growth media (e.g. blood agar), the inventive methods surprisingly allow the user to combine a suspension of red blood cells with a non-prehydrated nutrient medium comprising a gelling agent to produce an article capable of detecting and enumerating hemolysin producing microorganisms. The inventive methods further provide for the quantitation of different species and/or groups of hemolysin-producing microorganisms in a sample.

The term "source" is generally used to refer to the food or nonfood desired to be tested for microorganisms. The source can be a solid, a liquid, a semi-solid, a gelatinous material, and combinations thereof. In some embodiments, the source can be provided by a capture element that was used, for example, to collect the source from a surface of interest or from air. In some embodiments, the composition can include the capture element, which can be further broken apart (e.g., during an agitation or dissolution process) to enhance retrieval of the source and any microorganism of interest. The surface of interest can include at least a portion of a variety of surfaces, including, but not limited to, walls (including doors), floors, ceilings, drains, refrigeration systems, ducts (e.g., air ducts), vents, toilet seats, handles, doorknobs, handrails, bedrails (e.g., in a hospital), countertops, tabletops, eating surfaces (e.g., trays, dishes, etc.), working surfaces, equipment surfaces, clothing, etc., and combinations thereof. All or a portion of the source can be used in the method. When a portion of the source is used, this can sometimes be referred to as a "sample" of the source. However, the term "sample" is generally used herein to refer to the portion of volume or mass of material that is obtained from the source and is introduced into a culture plate device for the detection of microorganisms.

The term "food" is generally used to refer to a solid, liquid (e.g., including, but not limited to, solutions, dispersions, emulsions, suspensions, etc., and combinations thereof) and/or semi-solid comestible composition. Examples of foods include, but are not limited to, meats, poultry, eggs, fish, seafood, vegetables, fruits, prepared foods (e.g., soups, sauces, pastes), grain products (e.g., flour, cereals, breads), canned foods, milk, other dairy products (e.g., cheese, yogurt, sour cream), fats, oils, desserts, condiments, spices, pastas, beverages, water, animal feed, other suitable comestible materials, and combinations thereof.

The term "nonfood" is generally used to refer to sources of interest that do not fall within the definition of "food" and are generally not considered to be comestible. Examples of nonfood sources can include, but are not limited to, clinical samples, cell lysates, whole blood or a portion thereof (e.g., serum), other bodily fluids or secretions (e.g., saliva, sweat, sebum, urine), feces, cells, tissues, organs, biopsies, plant materials, nonpotable water, wood, soil, sediment, medicines, cosmetics, dietary supplements (e.g., ginseng capsules), pharmaceuticals, fomites, other suitable non-comestible materials, and combinations thereof.

"Sample acquisition device" is used herein in the broadest sense and refers to an implement used to collect a liquid, semisolid, or solid sample material. Nonlimiting examples of sample acquisition devices include swabs, wipes, sponges, scoops, spatulas, tongue depressors, filters, pipettes, pipette tips, and siphon hoses.

The term "fomite" is generally used to refer to an inanimate object or substrate capable of carrying infectious organisms and/or transferring them. Fomites can include, but are not limited to, cloths, mop heads, towels, sponges, wipes, eating utensils, coins, paper money, cell phones, clothing (including shoes), doorknobs, feminine products, diapers, etc., portions thereof, and combinations thereof.

The term "microorganism" is generally used to refer to any prokaryotic or eukaryotic microscopic organism capable of growing and reproducing in culture medium, including without limitation, one or more of bacteria (e.g., motile or vegetative, Gram positive or Gram negative), bacterial spores or endospores, fungi (e.g., yeast, filamentous fungi, fungal spores). In some cases, the microorganisms of particular interest are those that are pathogenic, and the term "pathogen" is used to refer to any pathogenic microorganism. Examples of pathogens can include, but are not limited to, members of the family Enterobacteriaceae, or members of the family Micrococcaceae, or the genera *Staphylococcus* spp., *Streptococcus*, spp., *Pseudomonas* spp., *Enterococcus* spp., *Salmonella* spp., *Legionella* spp., *Shigella* spp., *Yersinia* spp., *Enterobacter* spp., *Escherichia* spp., *Bacillus* spp., *Listeria* spp., *Campylobacter* spp., *Acinetobacter* spp., *Vibrio* spp., *Clostridium* spp., and *Corynebacteria* spp. Particular examples of pathogens can include, but are not limited to, *Escherichia coli* including enterohemorrhagic *E. coli* e.g., serotype O157:H7, *Pseudomonas aeruginosa, Bacillus cereus, Bacillus anthracis, Salmonella enteritidis, Salmonella typhimurium, Listeria monocytogenes, Clostridium botulinum, Clostridium perfringens, Staphylococcus aureus*, methicillin-resistant *Staphylococcus aureus, Campylobacter jejuni, Yersinia enterocolitica, Vibrio vulnificus, Clostridium difficile*, vancomycin-resistant *Enterococcus*, and *Enterobacter sakazakii*. Environmental factors that may affect the growth of a microorganism can include the presence or absence of nutrients, pH, moisture content, oxidation-reduction potential, antimicrobial compounds, temperature, atmospheric gas composition and biological structures or barriers.

A "filter" is generally used to describe the device used to separate the soluble matter (or soluble matter and relatively small insoluble matter) and solvent from the insoluble matter (or relatively large insoluble matter) in a liquid composition. Examples of filters can include, but are not limited to, a woven or non-woven mesh (e.g., a wire mesh, a cloth mesh, a plastic mesh, etc.), a woven or non-woven polymeric web (e.g., comprising polymeric fibers laid down in a uniform or non-uniform process, which can be calendered), a sieve, glass wool, a frit, filter paper, foam, etc., and combinations thereof.

Thin Film Culture Plate Devices

Figure 1:
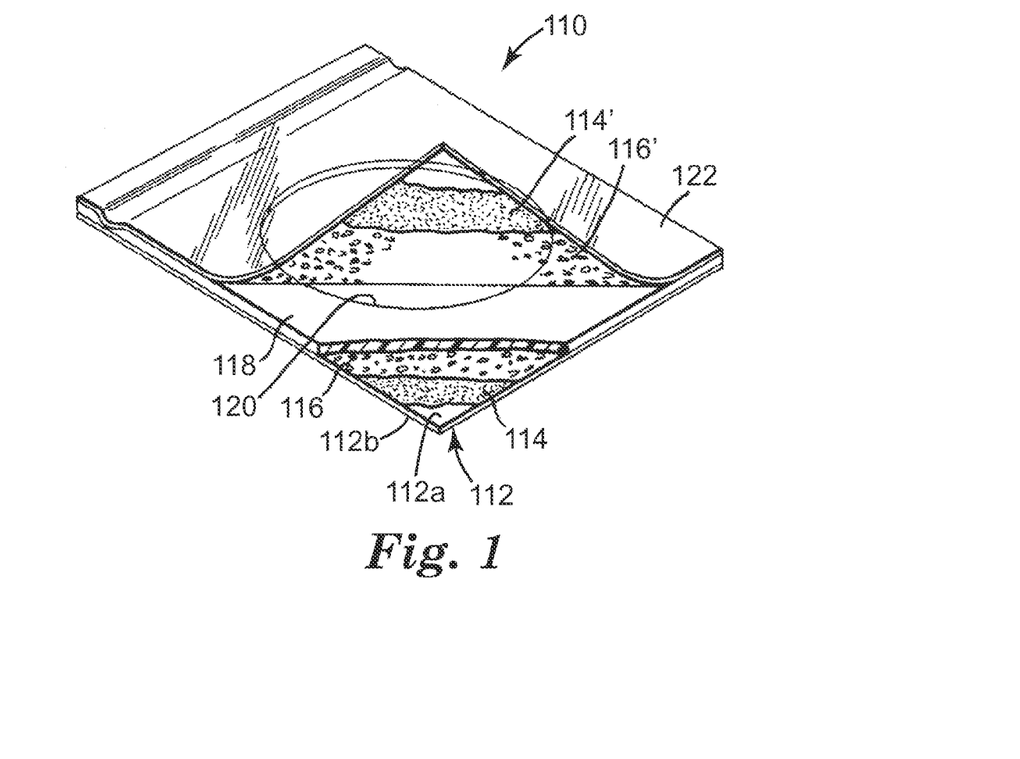
FIG. 1 is a top perspective view, partially in section, of an embodiment of a thin film culture plate device comprising a spacer.
Figure 2:
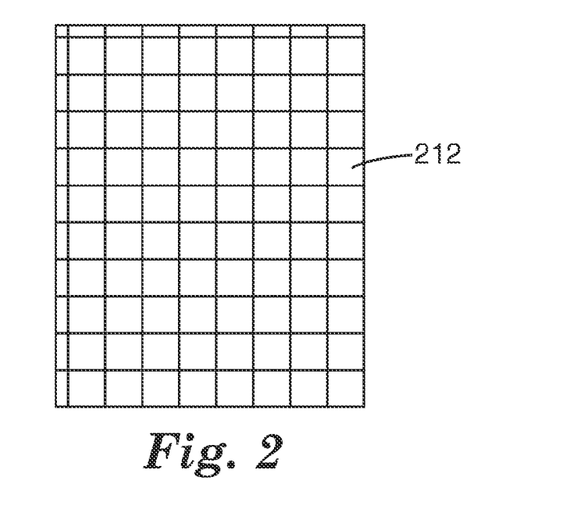
FIG. 2 is a top view of one embodiment of a self-supporting substrate comprising a grid pattern.

Articles of the present invention include thin film culture plate devices. Nonlimiting examples of such devices are described in U.S. Pat. Nos. 4,565,783; 5,137,812; 5,232,838; 5,681,712; and 6,331,429; which are each incorporated herein by reference in their entirety. FIG. 1 illustrates an embodiment of a thin film culture plate device in accordance with the present invention. The culture plate device 110 includes a body member comprising a self-supporting waterproof substrate 112 having upper and lower surfaces (112$a$ and 112$b$, respectively). Substrate 112 can be a relatively stiff film (e.g., polyester, polypropylene or polystyrene), which will not absorb or otherwise be affected by water. The substrate 112 may be either transparent or opaque, depending on whether one wishes to view bacterial colonies through the substrate. To facilitate the counting of bacterial colonies, the substrate 212 can have a grid pattern (e.g., squares) printed thereon, as shown in FIG. 2.

Referring back to FIG. 1, substrate 112 can be coated on its upper surface 112$a$ with a layer of an adhesive 114 which serves to hold the dry gelling agent and/or nutrients in a uniform layer for easy hydration. Adhesive 114 should be coated onto substrate 112 in a thickness which is preferably less than the diameter of the particles of the powdered gelling agent and/or nutrients. The object is to apply enough adhesive to adhere the particles to the substrate but not so much that the particles become completely embedded in the adhesive. A uniform layer of cold-water-soluble powder 116 is desired with sufficient surface area exposed for hydration. Also shown in FIG. 1 are optional adhesive 114' and cold-water-soluble powder 116' layers on cover sheet 122.

In some embodiments, adhesive 114 and/or adhesive 114' can comprise a water-based adhesive composition. Preferably, the layer of water-based adhesive is sufficiently transparent when wetted by an aqueous test sample to enable the viewing of the colonies of microorganisms. The water-based adhesive composition can incorporate one or more hydrophilic agents, including nutrients, selective agents, detection reagents (e.g., enzyme substrates, dyes), or combinations thereof. The specific nutrients, detection reagents, and/or selective agents used in the water-based adhesive composition will be apparent to those skilled in the art in view of the present specification depending upon the particular organisms to be grown and provided the nutrients, detection reagents, and or selective agents do not adversely affect the use of the red blood cells as an indicator for hemolysin-producing microorganisms (such as, for example, causing lysis or inhibiting the lysis of the red blood cells).

An exemplary useful class of hydrophilic selective agents include dyes that are metabolized by, or otherwise react with, growing microorganisms, and in so doing cause the microbial colonies to be colored or fluoresce for ease of detection and/or quantitation by a technician or by an automated reader. Nonlimiting examples of such dyes include triphenyltetrazolium chloride, p-tolyltetrazolium red, tetrazolium violet, veratryl tetrazolium blue, neutral red, phenol red, chlorophenol red, and 5-bromo-4-chloro-3-indolyl phosphate disodium salt. It will be appreciated that other suitable dyes can be used depending on the particular organism(s) to be identified.

In another embodiment of the invention, powder 116 may comprise nutrients but no gelling agent. Gelling agent may be desirable if one desires to visualize and/or isolate discrete bacteria colonies. In many microbiological tests, such as tests for bacteria identification or antibiotic susceptibility, broth media are used, and a viscous gel may not be necessary. In devices for carrying out such tests, the gelling agent may be omitted.

A buffering reagent, such as sodium carbonate, can be employed to provide a medium exhibiting a neutral pH and "Cab-O-Sil M-5" can be employed as a processing aid, as described in U.S. Pat. No. 4,565,783, which is incorporated herein by reference in its entirety. Of course, the particular coating mixture (e.g., nutrients, detection reagents, and/or gelling agents) used for powder 116 may be adjusted depending upon the type of microorganisms to be grown.

A non-limiting example mixture for powder to support the growth of a variety of microorganisms is as follows: 15 grams gum (e.g., a 1:1 mixture of Guar gum and Xanthan gum), 5 grams peptone, 2.5 grams yeast extract, 1 gram dextrose, 0.06 gram sodium carbonate, and 0.12 gram "Cab-O-Sil M-5" (a fumed silicon dioxide, commercially available from Cabot Corporation, Alpharetta, Ga.).

It is contemplated that articles of the present disclosure can include differential detection reagents. As used herein, "differential detection reagent" refers to a detection reagent added to the medium that will indicate the presence of certain microorganisms and not other microorganisms. Nonlimiting examples of differential detection reagents include dyes (e.g., stains, pH indicators, redox indicators), enzyme substrates (e.g., chromogenic or fluorogenic substrates for phosphatases, glycosidases, peptidases, nucleases, lipases, and the like), and specific nutrients (e.g., fermentable carbohydrates, amino acids) which, when metabolized by certain microorganisms, produce a detectable reaction (e.g., a pH change associated with a colony).

In some embodiments, one or more detection reagents can be added to the thin film culture plate device in the water-based composition that is coated onto the substrate. In some embodiments, one or more detection reagents can be added to the liquid sample that is added to the culture plate device. In some embodiments, one or more detection reagents can be added to the culture plate device, after hydration of the culture plate device. An example of a method involving the use of a differential detection reagent added to the culture plate device after hydration is the method wherein an article for the detection of thermonuclease is added to the culture plate device after incubation, such as described in U.S. Pat. No. 6,022,682 which is incorporated herein by reference in its entirety.

It is also contemplated within the scope of the invention that powder 116 may optionally include detection reagents necessary for carrying out certain biochemical tests for microorganism identification. Such detection reagents (e.g. a chromogenic enzyme substrate), which can undergo a color change, for example, when converted to a derivative of the detection reagent by a particular type of microorganism, may be included in the powder 116 or adhesive 114, provided the detection reagents do not adversely affect the use of the red blood cells as an indicator for hemolysin-producing microorganisms (such as, for example, causing lysis or inhibiting the lysis of the red blood cells).

In another embodiment of the invention, powder 116 may comprise a coating that includes a mixture of a gelling agent and a nutrient, a selective agent, and/or a detection reagent which has been dissolved or suspended in a solution, coated and dried onto substrate 112. In this embodiment, the coating is substantially water-free (i.e., the coating has a water content no greater than about the water content of the dehydrated coating once it has been permitted to equilibrate with the ambient environment).

As depicted in FIG. 1, the body member can include a spacer 118 applied to the upper surface of substrate 112, the spacer 118 comprising a circular aperture 120 cut through the center to expose the powder 116 on substrate 112. The walls of aperture 120 provide a well of predetermined size and shape to confine the medium following hydration. Spacer 118 should be thick enough to form a well of the desired volume, e.g., 1, 2 or 3 milliliters. Closed cell polyethylene foam is a preferred material for spacer 118, but any material which is hydrophobic (non-wetting), inert to microorganisms, and capable of withstanding sterilization may be used. In some embodiments (not shown), the spacer 118 can comprise a plurality of apertures 20 (e.g., 2, 3, 4, 5, 6, 7, 8, 9, 10, 12, 15, or 20 apertures), each of which can be inoculated with a distinct liquid sample.

Spacer 118 can include relatively thick designs, such as those described in U.S. Pat. No. 5,681,712, which is incorporated herein by reference in its entirety. One purpose of the thicker apertured spacer 118 is to locate and protect membranes (e.g. microporous filter membranes) placed in the aperture 120 of the spacer 118 (not shown). Another purpose of the thicker spacer 118 is to reduce or prevent contact by cover sheet 122 with the growing colonies of microorganisms (i.e., provide a "head space" between the growth surface and the cover sheet 122, which can also provide increased aeration for growing colonies of microorganisms).

The thickness of spacer 118 should be sufficient to enclose the liquid volume added to the culture plate device when the device is inoculated. Depending upon the thickness of the membrane, when used, the spacer can be at least about 0.5 mm thick, about 1 mm thick, about 1.5 mm thick and about 2 mm thick.

Figure 3:
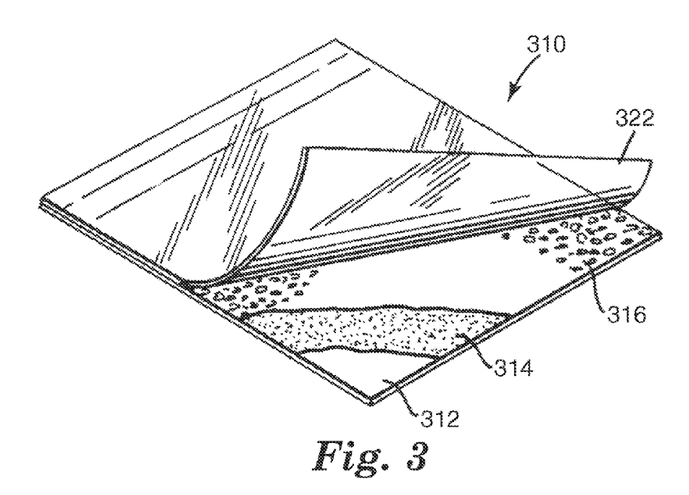
FIG. 3 is a top perspective view, partially in section, of an embodiment of a thin film culture plate device.

FIG. 3 shows another embodiment of a thin film culture plate device 310. This embodiment includes substrate 312, adhesive 314, cold-water-soluble powder 316, and cover sheet 322, as described in FIG. 1. In contrast to the culture plate device 110 of FIG. 1, the device 310 of FIG. 3 does not include a spacer to confine the sample during inoculation. A template, e.g., a weighted ring (not shown), may be applied temporarily to the outside of cover sheet 322, after closing, to confine the sample to a specific region while the cold-water-soluble powder 316 forms a gel. In some embodiments, the device 310 can be inoculated with a plurality (e.g., 2, 3, 4, 5, 6, 7, 8, 9, 10, 12, 15, or 20) of distinct liquid samples, using appropriate spacing and templates to confine the separate samples to distinct portions of the powder 316 of the culture plate device 310.

Figure 4:
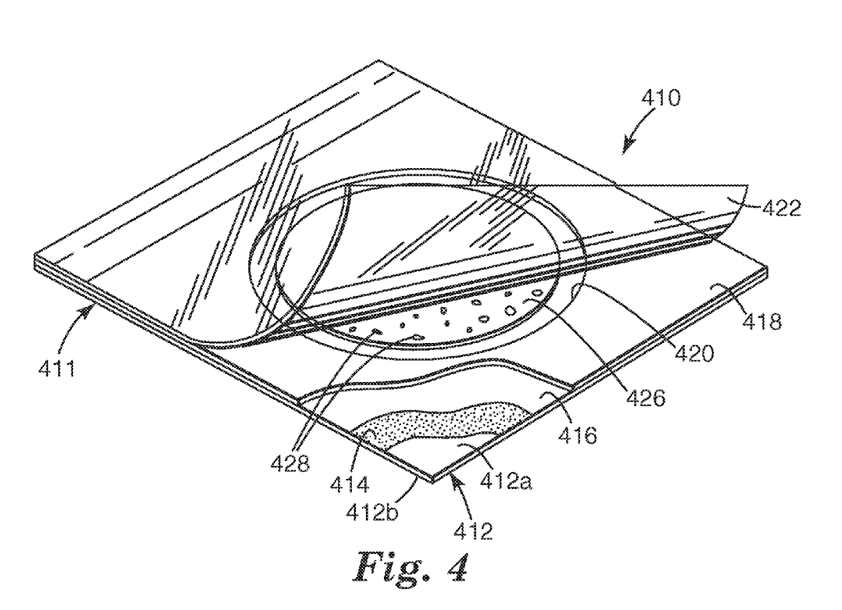
FIG. 4 is a top perspective view, partially in section, of an embodiment of a surface colony counting thin film culture plate device comprising a spacer and a capture element.

FIG. 4 illustrates another embodiment of a thin film culture plate device 410 in accordance with the present invention. Culture plate device 410 includes body member 411 comprising self-supporting substrate 412 having upper and lower surfaces 412a and 412b, respectively. Substrate 412 is coated on its upper surface 412a with a layer of adhesive 414. Cold-water-soluble powder 416, comprising one or more gelling agents, is adhered in a thin, relatively uniform layer to the adhesive 414. Once inoculated with an aqueous test sample (not shown), the layer of cold-water-soluble powder 416 quickly hydrates to form a reconstituted medium (not shown), which in turn is capable of growing microorganisms present either in a liquid inoculum or on the surface of a membrane such as a test sample microorganism filter (not shown). Spacer 418 partially covers substrate 412 and the surface of powder 416 and contains aperture 420. In addition, thin film culture plate device 410 optionally includes cover sheet 422, to cover the reconstituted medium formed after addition of the aqueous test sample. FIG. 4 also shows a capture element 426 and microorganism colonies 428 growing thereon. In the illustrated embodiment, capture element 426 is a microporous membrane through which a liquid sample has been filtered in order to trap any bacteria, if present in the sample, thereon.

Although the embodiments illustrated in FIGS. 1-4 have a cover sheet attached to the device, it is also contemplated within the scope of the invention that the powder-containing embodiments may be uncovered and simply placed in a sterile environment during storage and incubation.

It is possible to use air-permeable membrane layers in the devices of the present invention as described in U.S. Pat. No. 5,232,838. The air permeable layer can be "sandwiched" between the substrate and the cold-water-soluble powder, with an adhesive coating on both sides of the air-permeable membrane layer (not shown).

Capture Element

Culture plate devices of the present disclosure can be used with a capture element to detect hemolysin-producing microorganisms present in a sample. As used herein, "capture element" refers to an article that is used to capture and retain microorganisms that are present in a sample. In some embodiments, the capture elements can be contacted transiently with the thin-film culture plate devices disclosed herein. For example, the sample may be captured on one side of a surface filter and that side of the filter can be contacted with growth area of the thin-film culture plate device, and thereby transfer sample material to the growth area, before or after the culture plate device has been hydrated. The surface filter can then be removed from the device prior to hydrating the contacted growth area and/or after hydrating the contact growth area and prior to incubating the device. The capture element (e.g. a membrane filter) can be dimensioned to allow it to be placed into a thin film culture plate device of the present invention and, in certain preferred embodiments, the capture element remains in the thin film culture plate device during the incubation period for a sufficient period to allow for at least one cell division of the target microorganism. Placing the capture element into the culture plate device can bring the capture element in contact with a gelling agent and/or a nutrient medium, if present, in the culture plate device, allowing microorganisms to grow and/or proliferate. In some embodiments, the culture plate device is hydrated (e.g., inoculated with a sterile liquid or an unknown liquid sample) before the capture element is placed into the culture plate device. In some embodiments, the culture plate device is hydrated after the capture element is placed into the culture plate device.

Capture elements can be selected for their suitability with certain types of samples. For example, microporous membrane filters can be used as capture elements to retain microorganisms present in a liquid sample. The liquid sample can be passed through the filter and the microorganisms can be retained thereon. Microorganisms can be retained by, for example, physical entrapment or specific (e.g., antigen-antibody or receptor-ligand interaction) or nonspecific (hydrophobic adsorption) chemical interaction. Microporous membranes of the present disclosure, when present in the thin-film culture plate device, should permit the observation of a hemolytic reaction. Preferred microporous membrane filters become substantially transparent when wet.

Referring to the embodiment shown in FIG. 4, the test sample may comprise a liquid inoculum and/or a capture element 426 such as a microporous filter (e.g., a filter membrane) or a wipe device. Capture element 426 can be constructed from various membranes and/or films and can be used to capture microorganisms. In some embodiments, capture element 426 can provide a surface on which the colonies of microorganisms can be grown, detected and/or enumerated by the method and devices of the invention. Particularly suitable are known microporous filters which have been commonly used to separate small microorganism populations, such as bacteria from large fluid samples. Such filters are known to be placed on the surface of agar media and incubated to allow counting and evaluation of the filtered microbes. Suitable filters include the HAWG series, e.g., HAWG 047S6 type HA filter, available from Millipore Corp (Marlborough, Mass.). The microorganism filters described herein are generally relatively thin and may be provided in any desired 2-dimensional shape, e.g., as rectangles, as discs (including partial discs) and the like.

Microorganisms are separated by such filters with varying efficiency depending upon the sizes of the pores in the membranes. Bacteria are typically captured by filters having a mean pore diameter of less than about 1 µm, less than about 0.8 µm, preferably, less than about 0.45 µm, more preferably, equal to or less than about 0.2 µm. Filtration is carried out by conventional methods using gravity or vacuum-assisted methods with funnels and discs of suitable sizes. Membrane filters are preferably handled aseptically with tweezers. Membrane filters may be made by the user from commercially available materials or are provided in aseptic packages as separate entities or as parts of kits of the invention.

Wipe devices can be used as capture elements with the culture plate devices of the present disclosure. As used herein, a "wipe device" is an article that is configured for contacting a surface to obtain a sample of microorganisms disposed thereon. Wipe devices can include porous, nonwoven materials. Nonlimiting examples of wipe materials include paper (e.g., filter paper, cellulosic membrane filters), synthetic nonwovens (e.g., nylon or polyester nonwovens), polymeric or ceramic membranes (e.g., polycarbonate membranes, zirconia membranes), and micro structured films (e.g., microchannel-containing films such as those described in U.S. Pat. No. 7,223,364, which is incorporated herein by reference in its entirety). In some embodiments, the microchannel-containing films comprise through-holes that allow the passage of liquid (and solutes or small particles) from one major surface of the film to the other major surface. Wipe devices can include chemicals (e.g., surfactants), to improve wettability, or reagents (e.g., differential stains), provided the chemical or reagents do not adversely affect the use of the red blood cells as an indicator for hemolysin-producing microorganisms (such as, for example, causing lysis or inhibiting the lysis of the red blood cells). Wipe devices in general comprise chemicals in an amount that will not substantially inhibit the growth of microorganisms under the inoculation and incubation conditions described herein. In some embodiments, the capture elements are substantially transparent or become substantially transparent when wet, allowing for the visualization of a differential reaction, such as hemolysis, through the capture element.

Suitable capture elements include a particle, or a plurality of particles. The capture elements can include a means for coupling the capture element to microorganisms. Nonlimiting examples of particles include microspheres, microbeads, and the like. Such particles can be resin particles, for example, agarose, latex, polystyrene, nylon, polyacrylamide, cellulose, polysaccharide, or a combination thereof, or inorganic particles, for example, silica, aluminum oxide, or a combination thereof. Such particles can be magnetic, paramagnetic, superparamagnetic, or non-magnetic. Such particles can be colloidal in size, for example about 100 nm to about 10 microns ($\mu$m). Nonlimiting examples of such particles include superparamagnetic polymer particles sold under the trade names DYNABEADS (Invitrogen, Inc., Carlsbad, Calif.) and BIO-ADEMBEADS (Ademtech, Pessac, France). Particle capture elements may be incorporated into other structures, such as a microporous membrane.

There are a variety of means for coupling capture element (e.g., a particle) to a microorganism. In some embodiments, the means for coupling the capture element to the microorganism can include surface molecules or properties that promote nonspecific adsorption. For example, at least a portion of the capture element can have molecules on its surface that, under the proper conditions (e.g., high pH or low pH), become positively- or negatively-charged and nonspecifically adsorb to complementary-charged molecules associated with the surface of a microorganism.

Additionally, or alternatively, at least a portion of the capture element (e.g., a polystyrene particle) can have a hydrophobic surface which nonspecifically adsorbs to hydrophobic molecules associated with the surface of a microorganism. In some embodiments, the means for coupling a capture element to a microorganism may comprise a molecule that specifically binds to a microorganism through a receptor-ligand interaction. Such specific receptor-ligand interactions are well known in the art and include interactions between, for example, antibodies and their corresponding antigens, lectins and their corresponding carbohydrate binding partner, bacteriophage proteins and their corresponding phage receptors, and the like. It should be understood that the means for coupling a particle to a microorganism can also be used in conjunction with film or non-woven (e.g., filter) capture elements, as well as the particulate capture elements.

Samples

Hemolysin-producing microorganisms can be analyzed in a test sample that may be derived from any source, such as a physiological fluid, e.g., blood, saliva, ocular lens fluid, synovial fluid, cerebral spinal fluid, pus, sweat, exudate, urine, mucus, feces, lactation milk, or the like. Further, the test sample may be derived from a body site, e.g., wound, skin, nares, scalp, nails, etc.

Samples of particular interest include mucus-containing samples, such as nasal samples (from, e.g., anterior nares, nasopharyngeal cavity, nasal cavities, anterior nasal vestibule, etc.), as well as samples from the outer ear, middle ear, mouth, rectum, vagina, or other similar tissue. Examples of specific mucosal tissues include buccal, gingival, nasal, ocular, tracheal, bronchial, gastrointestinal, rectal, urethral, ureteral, vaginal, cervical, and uterine mucosal membranes.

Besides physiological fluids, other test samples may include other liquids as well as solid(s) dissolved in a liquid medium. Samples of interest may include process streams, water, soil, plants or other vegetation, air, surfaces (e.g., contaminated surfaces, floors, walls, instruments, bedding), and the like. Samples can also include cultured cells.

Various patient sampling techniques for the detection of microbes, such as *S. aureus*, on surfaces are known. Such sampling techniques are suitable for the methods of the present invention as well. For example, it is common to obtain a sample from wiping the nares of a patient. A particularly preferred sampling technique includes the subject's (e.g., patient's) anterior nares swabbed with a sterile swab or sampling device. For example, one swab is used to sample each subject, i.e., one swab for both nares. The sampling can be performed, for example, by inserting the swab dry or premoistened with an appropriate solution into the anterior tip of the subject's nares and rotating the swab for one or more complete revolutions along the nares' mucosal surface.

A wide variety of swabs or other sample collection devices are commercially available, for example, from Puritan Medical Products Co. LLC, Guilford, Me., under the trade designation PURE-WRAPS or from Copan Diagnostics, Inc. Corona, Calif., under the trade designation ESWAB, or from microRheologics, S.r.l., Brescia, IT, under the trade designation FLOCKEDSWAB. A sample collection means such as that disclosed, for example, in U.S. Pat. No. 5,879,635 (Nason) can also be used if desired. Swabs can be of a variety of materials including cotton, rayon, calcium alginate, Dacron, polyester, nylon, polyurethane, and the like.

The sample collection device (e.g., swab) can then be cultured directly, analyzed directly, or extracted (e.g., by washing, elution by vortexing) with an appropriate solution. Such extraction (i.e., elution) solutions typically include water and can optionally include a buffer and at least one surfactant, provided the surfactant do not adversely affect the use of the red blood cells as an indicator for hemolysin-producing microorganisms (such as, for example, causing lysis or inhibiting the lysis of the red blood cells). An example of an elution buffer includes, for example, phosphate buffered saline (PBS). The test sample (e.g., liquid) may be subjected to treatment prior to further analysis. This includes concentration, precipitation, filtration, centrifugation, dialysis, dilution, inactivation of natural components, addition of reagents, chemical treatment, etc.

Other sample collection devices, also referred to as "capture elements", can be used to collect samples from a surface or from liquid stream. In some embodiments, a capture element can be used to wipe a surface to collect a representative sample of microorganisms from the surface. Subsequently, the capture element can be transferred into a culture plate device, where it may remain during incubation and growth of the microorganisms. In some embodiments, a capture element can be used to filter microorganisms out of a liquid sample. After the filtration step, the capture element can be transferred into a culture plate device, where it may remain during incubation and growth of the microorganisms.

Methods for Detecting and Differentiating Hemolysin-Producing Microorganisms

Thin film devices disclosed herein can be used in methods to detect and differentiate hemolysin-producing microorganisms. The dry nutrients and/or gelling agent in the devices are hydrated with an aqueous solution to provide a nutrient environment in which the microorganisms can grow. The devices can be hydrated during the process of inoculating the device with the sample (i.e., the sample is an aqueous sample or the sample is suspended in an aqueous liquid, such as water or an aqueous buffer). Alternatively, the devices can be hydrated (e.g., using sterile water or aqueous buffer) prior to inoculation.

In some embodiments, the method comprises providing a sample, a thin film culture plate device as described herein, and a suspension of red blood cells (e.g., defibrinated blood, such as sheep blood). Optionally, in these embodiments, the culture plate device may comprise a detection reagent and/or a selective agent. The sample, which may be a liquid sample or a solid sample suspended in a liquid, is mixed with red blood cells before inoculating the culture plate device. The culture plate device cover sheet, if present, is lifted and the mixture comprising the sample and the red blood cells is inoculated (e.g., poured or pipetted) into the culture plate device. Alternatively, the sample and the red blood cells can be added to the culture plate device separately and quickly mixed (e.g., by stirring or swirling) in the device before the cold water-soluble gelling agent has hydrated completely. Optionally, a detection reagent and/or a selective agent may be added to the sample, the red blood cells, or the mixture of sample and red blood cells before or during the inoculation of the plate. The cover sheet, if present, is closed. A weighted plate or a specially-designed spreader can be placed on top of the cover sheet to spread the sample completely. The inoculated culture plate device is incubated for a period of time to allow the growth of microorganisms. Suitable incubation conditions (e.g., temperature, time) may be influenced by the particular organism(s) to be detected and such suitable conditions would be known by a person of ordinary skill in the art. After incubating the device for a period of time, the device is observed to detect the presence of microorganisms. Hemolysin-producing microorganisms can be detected by a hemolytic zone (e.g., clearing and/or discoloration) surrounding the microorganisms.

In some embodiments, the method comprises providing a sample, a thin film culture plate device as described herein, and a suspension of red blood cells. Optionally, in these embodiments, the culture plate device may comprise a detection reagent and/or a selective agent. The culture plate device cover sheet, if present, is lifted and an aqueous liquid comprising the red blood cells is transferred (e.g., poured or pipetted) into the device to hydrate the nutrient medium and/or gelling agent prior to the inoculation of the device with the sample. The aqueous liquid can be, for example, a suspension of red blood cells in a solution of buffered saline (e.g., phosphate buffered saline, PBS). Alternatively, an aqueous liquid (e.g., PBS) and red blood cells can be added to the device separately and mixed together before the cold water-soluble gelling agent has hydrated completely. After adding the aqueous liquid to the device, the cover sheet, if present, may be closed and the gelling agent is allowed to hydrate and form a gel, preferably at room temperature. The gel is allowed to form for at least several minutes; preferably, at least about 15 minutes; more preferably, at least about 30 minutes. After the gel has formed, the device may be held at temperatures between about 4-25° C. for a period of time before inoculating the device with the sample. When inoculating the prehydrated device, the coversheet, if present is lifted, exposing the hydrated gel. The sample is applied (e.g., pipetted, spread, or streaked) onto the hydrated gel comprising the red blood cells. If a liquid sample is applied, care must be taken to use a relatively small volume that can be absorbed readily by the hydrated gel. In some embodiments, the sample can be applied to the hydrated gel by contacting the gel with a capture element such as a membrane filter. Optionally, the capture element can remain in the culture plate device during at least a portion of the incubation period. The coversheet, if present, is closed. A weighted plate or a specially-designed spreader can be placed on top of the cover sheet to spread the sample completely. The device is incubated as described herein. After incubating the device for a period of time, the device is observed to detect the presence of microorganisms. Hemolysin-producing microorganisms can be detected as described herein.

In some embodiments, the method comprises providing i) any of the thin film culture plate devices described herein, ii) a nutrient medium for the growth of microorganisms, iii) an indicator system comprising a suspension of red blood cells, and iv) a sample suspected of containing microorganisms. Optionally, in these embodiments, the culture plate device may comprise a detection reagent and/or a selective agent. In some embodiments, the nutrient medium can provided as a dehydrated nutrient medium in culture plate device, as described herein. The culture plate device cover sheet, if present, is lifted and an aqueous mixture comprising the indicator system is contacted with the gelling agent in the culture plate device to form a hydrated gel. After contacting the aqueous mixture with the gelling agent, the cover sheet can be released to its original position. If the culture plate device does not comprise a spacer, such as the culture plate device 310, shown in FIG. 3, a weighted plate or a specially-designed spreader can be placed on top of the cover sheet to spread the sample over a defined area of the plate. The aqueous mixture used to form the hydrated gel comprises the indicator system (e.g., defibrinated sheep blood, at an effective concentration to observe a hemolytic reaction such as, for example, about 5% (v/v) to about 10% (v/v) blood in the aqueous mixture used to form the hydrated gel). Optionally, the aqueous mixture further can comprise the nutrient medium and/or a detection reagent and/or a selective agent. After the hydrated gel is formed, the sample material is contacted with the hydrated gel by, for example, pipetting and/or streaking the sample onto the surface of the gel. Alternatively, or additionally, at least a portion of the sample can be deposited into the culture plate device on a surface opposite the hydrated gel and the plate can be closed, thereby bringing the gel into contact with the sample. In some embodiments, the sample comprises a capture agent, such as particles or a membrane filter. In these embodiments, the capture agent can be placed into the culture plate device such that there is contact between the capture agent and the hydrated gel. After the sample has been contacted with the hydrated gel, the coversheet, if present, is closed. Optionally, trapped air bubbles may be expressed from the culture plate device by holding the plate against a flat surface and moving a smooth elongated object (e.g. a finger or a glass spreader) gently across the outer surface of the plate. The device is subsequently incubated as described herein. After incubating the device for a period of time, the device is observed to detect the presence of microorganisms. Hemolysin-producing microorganisms can be detected as described herein.

In some embodiments, the method comprises providing a sample, any of the thin film culture plate devices described herein, and a suspension of red blood cells. Optionally, in these embodiments, the culture plate device may comprise a detection reagent and/or a selective agent. The culture plate device cover sheet, if present, is lifted and the sample is spread (e.g., streaked or wiped) onto the dehydrated powder (e.g., part 116, 116', 316, or 416 of FIGS. 1, 3, and 4 described herein) to inoculate the culture plate device. After inoculation, an aqueous liquid (e.g., a buffer) comprising the suspension of red blood cells is transferred (e.g., poured or pipetted) into the device to hydrate the nutrient medium and/or gelling agent. Optionally, in these embodiments, the aqueous liquid comprising the suspension of red blood cells may further comprise a detection reagent and/or a selective agent. The coversheet, if present, is closed. A weighted plate or a specially-designed spreader can be placed on top of the cover sheet to spread the sample completely. The device is incubated as described herein. After incubating the device for a period of time, the device is observed to detect the presence of microorganisms. Hemolysin-producing microorganisms can be detected as described herein.

In some embodiments, the method comprises providing a capture element comprising a sample, any of the thin film culture plate devices described herein, and a suspension of red blood cells. Optionally, in these embodiments, the culture plate device may comprise a detection reagent and/or a selective agent. The culture plate device cover sheet, if present, is lifted and the capture element (e.g., a membrane filter, a wipe, particles, or a swab) are contacted (e.g., touched, wiped, and/or streaked) on the growth area of the culture plate device. Optionally, the capture element may be placed into the culture plate device and remain in the device during inoculation and at least part of the incubation period. An aqueous liquid comprising the red blood cells is transferred into the device as described herein to hydrate the nutrient medium and gelling agent. The cover sheet, if present is closed. A weighted plate or a specially-designed spreader can be placed on top of the cover sheet to spread the sample completely. The inoculated device is incubated for a period of time. After the incubation period, the device is observed to detect the presence of microorganisms. Hemolysin-producing microorganisms can be detected as described herein.

The thin film devices can further be used in methods to enumerate hemolysin-producing microorganisms. After inoculation, the culture plate device is then incubated for a predetermined period of time. Bacterial colonies growing in or on the medium or capture element can be counted through the cover film, if present. In some embodiments, the microorganisms can be counted using an automated system, such as an automated colony counter. It is contemplated that a hemolytic zone surrounding a hemolysin-producing colony in a thin film culture plate device can be imaged by an automated colony counter, thereby permitting automated enumeration of hemolysin-producing microorganisms in thin-film culture plate devices including an indicator system comprising red blood cells.

Hydrophilic agents (e.g., a nutrient, an antibiotic, a detection reagent) can be added to an inoculated/hydrated culture plate device by contacting a liquid, semi-solid solution or a dehydrated article (e.g., coated, dried substrate) with the hydrated nutrient medium in the culture plate device after the culture plate device has been inoculated. The dehydrated article may be a partially-dehydrated article. The substrate can comprise a plastic film, a microporous membrane, a cellulosic material, or a nonwoven material.

Differential detection reagents, if present, can be used to distinguish between and provide a differential count of different groups or species of microorganisms. For example, enzyme substrates can be used as detection reagents to differentiate between colonies containing staphylococci and colonies containing *Bacillus* species or other microorganisms. U.S. Pat. No. 5,837,482, which is incorporated herein by reference in its entirety, describes an indicator system using an indolyl-glucopyranoside enzyme substrate to detect non-staphylococcal microorganisms and Baird-Parker differential reagents (e.g., Egg Yolk-Tellurite suspension) to detect staphylococcal microorganisms. U.S. Pat. No. 5,635,367, which is incorporated herein by reference in its entirety, describes an indicator system using an indolyl-glucopyranoside enzyme substrate to detect non-staphylococcal microorganisms and an indolyl-phosphate enzyme substrate to detect staphylococcal microorganisms.

Colonies can be picked from the culture plate device to perform differential tests. Colonies can be tested individually or they can be grouped, or "pooled", for differential testing. Colonies can be "pooled", for example, by picking two or more colonies from the device, mixing them together, and performing a differential test simultaneously on microorganisms from the two or more colonies. The differential tests can include, for example, staining tests (e.g. Gram stain, spore stain, immunochemical staining), enzymatic (e.g., a DNase test, a TNase test), surface receptor recognition tests (e.g., coagulase test or clumping factor test), genetic tests (e.g., amplification tests, such as PCR and rtPCR; nucleic acid sequencing; or hybridization assays (e.g., FISH assays)), immunoassay tests (e.g., ELISA, immunodiffusion, immunochromatography), or biochemical tests (e.g., coagulase test, catalase test, carbohydrate fermentation (e.g., mannitol fermentation), lipid analysis)

Kits of the Invention

Kits provided by the present invention include two or more parts. One part includes a thin film culture plate device described herein. A second part of the kit includes a suspension of red blood cells (such as, for example, defibrinated blood). A third part of each kit may be selected from the group of accessory articles consisting of a membrane filter, a pipette, a spreader, a glove, a sample acquisition device, a capture element, a sample-suspending medium, a reagent, and any two or more of the foregoing accessory articles.

Membrane filters preferably should be of a shape and size that is suitable to fit into the culture plate device of the kit. If the culture plate device comprises a spacer as described herein, preferably, the membrane filter is dimensioned to fit in the aperture of the spacer. Filters of different kinds can be provided with a kit, or multiple kits can contain various filters. The filters are optional and, preferably, provided in aseptic condition such as a polyethylene coated paper package which has been sterilized by gamma irradiation, ethylene oxide or other sterilization. Alternatively the filters may be nonsterile units which are to be sterilized by the user.

Suitable pipettes and spreaders can be made from, for example, plastic or glass. The pipettes and spreaders can be provided in a pre-sterilized condition or can be provided in a nonsterile condition. The pipettes and spreaders can be disposable after a single use or can be resterilized for multiple uses. "Pipettes", as used herein include volumetric pipettes with at least one gradation mark corresponding to a known volume and pipette tips, which can be used with a volumetric pipetting device. The kit can contain a package of hydrophilic agents. The hydrophilic agents are preferably contained in a sterile package for example a foil package such as those conventionally used in the pharmaceutical industry. An example of such a package is used for NITRO-BID Ointment (Marlon Laboratories, Inc., Kansas City, Mo.).

The nutrients and/or selective agents included in the kits may be incorporated into the adhesive and/or powder compositions, as discussed above. The selection of the hydrophilic agents useful and necessary in the kits depends upon the microorganism to be evaluated. Other criteria for selection of components of a kit will be short and long term chemical compatibility of the hydrophilic agents and compatibility (i.e., lack of significant interference with the detection of a hemolysin-producing microorganism, as described herein) of the hydrophilic agents with the red cells.

The invention will be further illustrated by reference to the following non-limiting Examples. All parts and percentages are expressed as parts by weight unless otherwise indicated. Unless specified otherwise, all reagents were obtained from Sigma Chemical Company (St. Louis, Mo.).

EXAMPLES

Example 1

Detection of Hemolysis in Thin Film Culture Plate Devices Containing a Red Blood Cell Indicator and a Sample Containing Microorganisms Phosphate buffered saline (PBS) was obtained as a 10× concentrate (OMNIPUR 6505, from EMD Chemicals, Gibbstown, N.J.), diluted with deionized water and filter-sterilized (0.22 μm) before use. Remel R54012 defibrinated sheep blood was obtained from Thermo Fisher Scientific, Lenexa, Kans.). Blood agar plates, containing 5% sheep blood, were obtained from Hardy Diagnostics (Santa Maria, Calif.). *Staphylococcus aureus* ATCC strain 25923 was obtained from the American Type Culture Collection (Manassas, Va.). Petrifilm Aerobic Count (PAC) and Petrifilm Staph Express (PSTX) plates were obtained from 3M Company (St. Paul, Minn.).

Preparation of Indicator Blood Cell Suspensions

Sheep red blood cells were mixed with a PBS concentrate to make suspensions of red blood cells (5% v/v, and 10% v/v, respectively) in 1×PBS. For example, 10 mL of PBS concentrate was mixed with 80 mL of deionized water and the (1.1×PBS) mixture was filter-sterilized. Ten milliliters of defibrinated sheep blood was mixed with the 1.1×PBS to yield 1×PBS containing 10% (v/v) sheep blood. Alternatively, 10 mL of PBS concentrate was mixed with 85 mL of deionized water and the (1.05×PBS) mixture was filter-sterilized. Five milliliters of defibrinated sheep blood was mixed with the 1.05×PBS to yield 1×PBS containing 5% (v/v) sheep blood. Control PBS was prepared at 1× concentration without sheep red blood cells. All mixtures were stored at 4° C. and were used within about 24 hours after they were made.

Sheep red blood cells were mixed with a sterile tryptic soy broth (TSB) concentrate similarly. That is, a 1.1× concentrate of TSB was prepared and autoclaved. Ten milliliters of sheep blood was added to 90 milliliters of the TSB concentrate to prepare the 10% sheep blood suspension. Five milliliters of sterile water and 5 milliliters of sheep blood were added to the TSB concentrate to prepare the 5% sheep blood suspension. Ten milliliters of sterile water was added to the TSB concentrate to prepare the TSB control (0% sheep blood). All mixtures were stored at 4° C. and were used within about 24 hours after they were made.

Preparation of Bacterial Suspensions

*S. aureus* ATCC strain 25923 was inoculated into a 1-mL tube of sterile tryptic soy broth and was incubated overnight at 37° C. The bacteria were pelleted by centrifugation, washed twice in PBS, and resuspended in an equal volume of sterile PBS. The suspension was used to prepare six serial 10-fold dilutions ($10^{-1}$ to $10^{-6}$) in sterile PBS.

Preparation of Nutrient-Free Plating Devices

Plating devices were constructed essentially as shown in FIG. 1 with the notable exception that the cold-water-soluble powder 116, shown adhered to adhesive 114, was omitted. The spacer consisted of 20 mil (0.5 mm) thickness closed-cell polyethylene foam obtained from American Fuji Seal (Bardstown, Ky.). The substrate consisted of 5 mil (0.13 mm) thickness polyester film. The cover sheet consisted of 1.6 mil (0.4 mm) thickness biaxially-oriented polypropylene (BOPP) film. Adhesive was coated onto one side of the BOPP film. A mixture of xanthan, locust bean, and guar gum powders (1:1: 0.5 ratio) was coated onto the adhesive. Adhesive was coated onto one side of the spacer and 2⅜ inch-diameter (60.3 mm) circular apertures were die-cut from the spacer material. The powder-coated cover sheet was adhered to the spacer along one edge of the plate using ½-inch wide (12.3 mm) double-sided adhesive tape (3M Company). Individual plates were approximately 4 inches (102 mm) long and 3 inches (76 mm) wide, with the aperture approximately in the center of the plate. The assembled plates were decontaminated by exposure to gamma irradiation (20 kGy).

Inoculation and Incubation of Plates

Blood agar plates were inoculated by spreading one-hundred microliters of the $10^{-6}$ dilution was spread over the surface of the plates. The $10^{-4}$ and $10^{-5}$ dilutions of the bacterial suspensions were further diluted 1:100 into the PBS/sheep blood suspensions and one milliliter aliquots of the resulting suspension were inoculated into PAC and PSTX plates according to the manufacturer's directions. The $10^{-4}$ and $10^{-5}$ dilutions of the bacterial suspension were further diluted 1:100 into the TSB/sheep blood suspensions and one milliliter aliquots of the resulting suspensions were inoculated into nutrient-free plating devices using the inoculation method for the PSTX plate (note: the TSB and/or blood provides the nutrients for the microorganisms to grow in the nutrient-free plating devices). One-milliliter portions of all diluent and broth controls were inoculated into PAC plates to check for sterility. After inoculation, plates were incubated at 35° C. for 48 hours. Plates that had colony counts numbering between 25-250 colonies were observed for the presence or absence of observable hemolytic zones as evidenced by a clearing of the red blood cells around the colonies. Plates were observed for colony color and morphology and hemolytic zones after 24 and 48 hours of incubation.

Colony growth was visible on PAC and PSTX plates after 24 hours of incubation, and on the nutrient-free plating devices after 48 hours of incubation. Colony color was red on PAC plates, purple on PSTX plates, and yellowish-white on the nutrient-free plating devices. The growth area appeared pink in the PAC and nutrient-free plating devices inoculated with the suspensions containing 5% sheep blood. The growth area appeared red in the PAC and nutrient-free plating devices inoculated with the suspensions containing 10% sheep blood. The growth area appeared light-brown and brown in the PSTX plates inoculated with the suspensions containing 5% and 10% sheep blood, respectively, indicating that the blood may have been hemolyzed or plasmolyzed by a component of the selective medium in the plates. Hemolytic zones (i.e., clearing or lighter color in the area surrounding colonies) were visible in the PAC plates within 24 hours after inoculation and were visible in the nutrient-free plating devices within 48 hours after inoculation. Hemolytic zones were not visible in PSTX plates within 48 hours after inoculation. All diluent and broth controls were negative for growth on AC plates at 24 and 48 hours.

Example 2

Differentiation of *S. aureus* and *S. epidermidis* Colonies Grown in a Thin-Film Culture Plate Device with a Red Blood Cell Indicator

*Staphylococcus epidermidis* ATCC 12228 was obtained from the American Type Culture Collection (Manassas, Va.). Bacterial cultures (individual cultures of *S. aureus* ATCC 25923 and *S. epidermidis* ATCC 12228), indicator blood cell suspensions, and nutrient-free plating devices were prepared as described in Example 1. Two sets of plates were inoculated as described in Example 1—one set was inoculated with *S. aureus* and the other was inoculated with *S. epidermidis*.

*S. aureus* and *S. epidermidis* colonies were visible within 24 hours after inoculating the PAC plates. Hemolytic zones were visible surrounding the *S. aureus* colonies within 24 hours after inoculating the PAC plates. The hemolytic zones surrounding *S. aureus* colonies were larger after 48 hours of incubation. No hemolytic zones were observed surrounding *S. epidermidis* after 24 or 48 hours of incubation.

S. aureus colonies were visible within 24 hours after inoculating the PSTX plates. A few colonies of S. epidermidis were visible on the plate with the highest dilution within 48 hours after inoculating the PSTX plates. No hemolytic zones were visible surrounding any colonies in PSTX plates after 24 or 48 hours of incubation.

S. aureus colonies were visible within 24 hours after inoculating the strain into the nutrient-free plating devices. S. epidermidis colonies were visible in the nutrient-free plating devices within 48 hours of incubation. Hemolytic zones were observed surrounding the S. aureus colonies after 24 and 48 hours of incubation. No hemolytic zones were observed after 24 or 48 hours of incubation of the S. epidermidis strain.

Example 3

Detection of Hemolysis by Antibiotic-Resistant Microorganisms in Thin Film Culture Plate Devices Phosphate buffered saline with sheep blood was prepared as described in Example 1. Antibiotic stock solutions (3 mg/mL and 4 mg/mL) were individually prepared in DI water. The solutions were filter-sterilized. The antibiotics included cefoxitin, cefazolin, and cefuroxime. The antibiotics were diluted 1:1000 into PBS/sheep blood aliquots to achieve final antibiotic concentrations of 3 μg/mL and 4 μg/mL, respectively.

Bacterial strains used in this Example include methicillin-sensitive S. aureus (strain 25923, obtained from ATCC), methicillin-resistant S. aureus (strain 565, clinical isolate), methicillin-sensitive S. epidermidis (strain 25, clinical isolate), and methicillin-resistant S. epidermidis (strain 497, clinical isolate). Each strain was grown overnight in tryptic soy broth, pelleted, and resuspended in sterile PBS, as described in Example 1. The bacterial suspensions were subjected to two serial 1:100 dilutions in sterile PBS. The diluted suspensions were then further subjected to a 1:100 dilution into each of the respective PBS/sheep blood mixtures containing an antibiotic. One milliliter of each final suspension; containing sheep blood, microorganisms, and an antibiotic in PBS; was into a PAC plate as described above. The plates were incubated at 35° C. for 48 hours. Each plate was checked for colony growth and hemolytic zone after 24 and 48 hours of incubation. The results are summarized in Table 1.

Example 4

Detection of Hemolysis in Thin Film Culture Plate Devices Prehydrated with a Buffer Containing a Red Blood Cell Indicator Phosphate buffered saline with sheep blood was prepared as described in Example 1. Filters used for this example included pre-sterilized S-Pack 0.45 μM filter (47 mm diameter filter, product number HAWG047S6; Millipore, Billerica, Mass.) or DURAPORE 0.22 μM filter (hydrophilic polyvinylidene fluoride (47 mm diameter, product number GVWP04700; Millipore). DURAPORE filters were sterilized by autoclaving according to the manufacturer's instructions. The filters were placed into a sterile, reusable filter unit and, after the filtration step; the filters were aseptically transferred to the PAC plates, as described below, using sterile forceps.

Sets of PAC plates were prehydrated according to the manufacturer's instructions with PBS (control) and PBS containing 10% sheep blood, respectively. Briefly, one-milliliter of the prehydrating solution was inoculated into the plates and a plastic spreading device was used to distribute the liquid in a circular (5.1 mm diameter) area of the plate. The plates were allowed to stand on a flat surface at room temperature for 30 minutes, then placed into a resealable plastic bag and stored at 4° C. until use. Typically, the plates were used two days after prehydration. The prehydrated plates were allowed to warm to room temperature before they were inoculated.

Bacteria (S. aureus strain 565 and S. epidermidis strain 12228) were grown overnight, washed, and resuspended in PBS as described in Example 1. Each washed bacterial suspension was subjected to four 1:10 dilutions in sterile PBS, followed by a 1:5 dilution and two 1:2 dilutions. Thus, the final three dilutions represented cumulative dilutions (or the washed bacterial suspension) of $2\times10^{-5}$, $1\times10^{-5}$, and $5\times10^{-6}$, respectively. From each of the final three dilutions, a 10 microliter aliquot was used to inoculate one of the prehydrated PAC plates as described below (Direct Inoculation). From each of the final three dilutions, an additional 1:100

TABLE 1

Detection of hemolytic activity in thin film culture plate devices. All diluents contained 10% sheep blood in PBS. Blank diluent contained no antibiotic. Cefo, Cefa, and Cefu denote cefoxitin, cefazolin, and cefuroxime, respectively. Growth and hemolysis results are reported as present (+) or absent (−) at 24 and 48 hours, with the respective observations separated by a forward slash.

| Diluent | S. aureus strain 25932 | | S. aureus strain 565 | | S. epidermidis strain 25 | | S. epidermidis strain 497 | |
|---|---|---|---|---|---|---|---|---|
| | Growth | Hemolysis | Growth | Hemolysis | Growth | Hemolysis | Growth | Hemolysis |
| Blank | +/+ | −/+ | +/+ | +/+ | +/+ | −/− | +/+ | −/− |
| Cefo(3) | −/− | −/− | +/+ | +/+ | −/− | −/− | +/+ | −/− |
| Cefo(4) | −/− | −/− | +/+ | +/+ | −/− | −/− | +/+ | −/− |
| Cefa(3) | −/− | −/− | −/+ | −/+ | −/− | −/− | +/+ | −/− |
| Cefa(4) | −/− | −/− | −/+ | −/+ | −/− | −/− | +/+ | −/− |
| Cefu(3) | −/− | −/− | +/+ | +/+ | −/− | −/− | +/+ | −/− |
| Cefu(4) | −/− | −/− | +/+ | +/+ | −/− | −/− | +/+ | −/− | dilution was made and 10 milliliters of the resulting suspension was filtered through a sterile membrane filter, which was subsequently used to inoculate one of the prehydrated PAC plates as described below (Filter Inoculation).

In the direct inoculation method, all procedures were performed with the plate resting on a bench top with the cover sheet oriented on the upper side. While holding an edge of the coated bottom film, the cover sheet was lifted such that the prehydrated gel remained separated from the bottom film and remained on the coversheet (as illustrated in Step 1 of the "Direct Contact" method of the 3M PETRIFILM Plates Environmental Monitoring Procedures Brochure (Publication Number 70-2008-2412-9, 3M Company). The plate was held open essentially as described in Step 2 of the Air Sampling Method of the Environmental Monitoring Procedures brochure described above. After the plate was opened, the 10-microliter inoculum was pipetted onto the prehydrated gel and a sterile plastic spreader was used to distribute the inoculum over the entire surface of the gel. The cover sheet was then gently rolled onto the substrate to close the plate. After closing the plate, a gloved finger was gently slid over the surface of the cover sheet to ensure contact between the prehydrated gel and the substrate and to express any air bubbles that were trapped between the gel and the substrate.

In the filter inoculation method, all procedures were performed with the plate resting on a bench top with the cover sheet oriented on the upper side. The cover sheet was lifted as described in the "direct inoculation" method. The filter was placed on the substrate with the upper surface of the filter (i.e., the surface that was uppermost during the filtration step) facing away from the substrate (i.e., facing toward the prehydrated gel). The coversheet was rejoined to the substrate such that prehydrated gel gently rolled onto the filter. After closing the plate, a gloved finger was gently slid over the surface of the cover sheet to ensure contact between the filter and the prehydrated gel and to express any air bubbles that were trapped between the gel and the filter.

All plates were incubated at 35° C. and were visually observed after 20 and 40 hours of incubation, respectively. Uninoculated PBS was also filtered on sterile filters and plated onto each type of prehydrated plate as a control. The observations are presented in Tables 2 and 3.

TABLE 2

Detection of hemolysis by *staphylococcal* strains grown in a prehydrated plate containing indicator red blood cells. Growth and hemolysis results are reported as present(+) or absent (−). Plates were inoculated using the direct inoculation method described in Example 4. The PBS control plate did not contain a blood cell indicator and, thus, no hemolytic reaction was recorded.

| | *S. epidermidis* strain 12228 | | | | *S. aureus* strain 565 | | | |
|---|---|---|---|---|---|---|---|---|
| Prehydration | 20 hours | | 40 hours | | 20 hours | | 40 hours | |
| Medium | Growth | Zone | Growth | Zone | Growth | Zone | Growth | Zone |
| PBS | + | n/a | + | n/a | + | n/a | + | n/a |
| PBS/ 10% Blood | + | − | + | − | + | + | + | + |

TABLE 3

Detection of hemolysis by *staphylococcal* strains on a membrane filter placed into a prehydrated plate containing indicator red blood cells. Growth and hemolysis results are reported as present (+) or absent (−). Control plates did not contain blood cells in the prehydrated gel. The control plates did not contain a blood cell indicator and, thus, no hemolytic reaction was recorded.

| | *S. epidermidis* Strain 12228 | | | | *S. aureus* strain 565 | | | |
|---|---|---|---|---|---|---|---|---|
| Filter/ | 20 hours | | 40 hours | | 20 hours | | 40 hours | |
| % SRBC | Growth | Zone | Growth | Zone | Growth | Zone | Growth | Zone |
| HAWG/ Control | + | n/a | + | n/a | + | n/a | + | n/a |
| HAWG/ 10% blood | + | − | + | − | + | − | + | − |
| GVWP/ Control | + | n/a | + | n/a | + | n/a | + | n/a |
| GVWP/ 10% blood | + | − | + | − | + | − | + | − |

The present invention has now been described with reference to several specific embodiments foreseen by the inventor for which enabling descriptions are available. Insubstantial modifications of the invention, including modifications not presently foreseen, may nonetheless constitute equivalents thereto. Thus, the scope of the present invention should not be limited by the details and structures described herein, but rather solely by the following claims, and equivalents thereto.

What is claimed is:

1. A method for detecting microorganisms, the method comprising:
    providing i) a thin film culture plate device comprising a dry, cold water-soluble gelling agent, ii) a nutrient medium for the growth of microorganisms, iii) an indicator system comprising a suspension of red blood cells, and iv) a sample suspected of containing microorganisms;
    contacting the sample, nutrient medium, and indicator system with the dry, cold water-soluble gelling agent to form an aqueous mixture comprising the gelling agent and the sample;
    incubating the mixture for a period of time; and
    detecting a microorganism, wherein the detecting a microorganism comprises detecting a hemolytic reaction.

2. The method of claim 1, wherein detecting a microorganism comprises counting colonies of microorganisms.

3. The method of claim 2, wherein counting colonies comprises enumerating one or more types of microorganisms.

4. The method of claim 3, wherein the one or more types of microorganisms are enumerated on the basis of a colony color, fluorescence, size, shape, hemolytic reaction or a combination of any two or more of the foregoing.

5. The method of claim 1, further comprising a step wherein a portion of at least one colony is subjected to a supplemental test.

6. The method of claim 5, wherein the portion of at least one colony is removed from the nutrient medium to conduct the supplemental test.

7. The method of claim 1, wherein the sample comprises a capture element.

8. A method for detecting microorganisms, the method comprising:
    providing i) a thin film culture plate device comprising a dry, cold water-soluble gelling agent, ii) a nutrient medium for the growth of microorganisms, iii) an indicator system comprising a suspension of red blood cells, and iv) a sample suspected of containing microorganisms;
    contacting the dry, cold water-soluble gelling agent with an aqueous mixture comprising the indicator system and the nutrient medium to form a hydrated gel;
    contacting the hydrated gel with the sample;
    incubating the device comprising the hydrated gel and the sample for a period of time; and
    detecting a microorganism, wherein the detecting a microorganism comprises detecting a hemolytic reaction.

9. The method of claim 8, where contacting the hydrated gel with the sample comprises streaking a portion of the sample onto the hydrated gel.

* * * * *

UNITED STATES PATENT AND TRADEMARK OFFICE
CERTIFICATE OF CORRECTION

| | | |
|---|---|---|
| PATENT NO. | : 8,828,682 B2 | Page 1 of 1 |
| APPLICATION NO. | : 13/133456 | |
| DATED | : September 9, 2014 | |
| INVENTOR(S) | : Patrick A. Mach and Michelle L. Rosauer | |

It is certified that error appears in the above-identified patent and that said Letters Patent is hereby corrected as shown below:

In the Specification

Column 10,
Line 44, "micro structured" should read --microstructured--.

Signed and Sealed this
Twenty-ninth Day of September, 2015

Michelle K. Lee
*Director of the United States Patent and Trademark Office*